USO10213186B2

United States Patent
Inoue et al.

(10) Patent No.: US 10,213,186 B2
(45) Date of Patent: Feb. 26, 2019

(54) IMAGING APPARATUS FOR DIAGNOSIS AND PROBE

(71) Applicant: TERUMO KABUSHIKI KAISHA, Shibuya-ku (JP)

(72) Inventors: Koichi Inoue, Odawara (JP); Junya Furuichi, Hadano (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1115 days.

(21) Appl. No.: 14/488,518

(22) Filed: Sep. 17, 2014

(65) Prior Publication Data
US 2015/0005615 A1 Jan. 1, 2015

Related U.S. Application Data

(63) Continuation of application No. PCT/JP2013/001866, filed on Mar. 19, 2013.

(30) Foreign Application Priority Data

Mar. 29, 2012 (JP) ................................. 2012-076730

(51) Int. Cl.
 *A61B 8/00* (2006.01)
 *A61B 5/0295* (2006.01)
 (Continued)

(52) U.S. Cl.
 CPC ............ *A61B 8/445* (2013.01); *A61B 5/0295* (2013.01); *A61B 5/1128* (2013.01); *A61B 8/065* (2013.01);
 (Continued)

(58) Field of Classification Search
 CPC ....... A61B 8/445; A61B 8/065; A61B 8/4461; A61B 8/12; A61B 8/5223; A61B 5/1128;
 (Continued)

(56) References Cited

U.S. PATENT DOCUMENTS

| 4,873,990 A * | 10/1989 | Holmes .................. A61B 5/036 600/488 |
| 2011/0137140 A1 | 6/2011 | Tearney et al. |
| 2011/0178413 A1 * | 7/2011 | Schmitt ................ A61B 5/0066 600/478 |

FOREIGN PATENT DOCUMENTS

| EP | 1849409 A1 | 10/2007 |
| JP | 2003-525067 A | 8/2003 |

(Continued)

OTHER PUBLICATIONS

Takashi Akasaka, Application of a Pressure Guide Wire Combined with Thermography in the Assessment of Coronary Stenotic Lesions, Medical and Biological Engineering 43(1), pp. 24-31, 2005 (month unknown).

(Continued)

*Primary Examiner* — Jonathan Cwern
(74) *Attorney, Agent, or Firm* — Buchanan Ingersoll & Rooney PC

(57) ABSTRACT

An imaging apparatus for diagnosis is provided in which a simpler configuration enables an anatomical technique and a physiological technique to be used in combination. The imaging apparatus for diagnosis disclosed herein includes a first calculator for calculating a parameter indicating each deformation degree of measurement slit portions, by using a tomographic image including the measurement slit portions which are disposed at different positions in an axial direction of a probe unit and whose cross-sectional shape is deformed in response to a pressure applied to the probe unit, and a second calculator for calculating a value corresponding to a myocardial fractional flow reserve, based on the calculated parameter.

17 Claims, 11 Drawing Sheets

(51) Int. Cl.
*A61B 5/11* (2006.01)
*A61B 8/06* (2006.01)
*A61B 8/12* (2006.01)
*A61B 8/08* (2006.01)
A61B 5/0215 (2006.01)
A61B 5/02 (2006.01)
A61B 5/026 (2006.01)
A61B 5/027 (2006.01)
A61B 5/029 (2006.01)
A61B 5/00 (2006.01)

(52) U.S. Cl.
CPC .............. *A61B 8/12* (2013.01); *A61B 8/4461* (2013.01); *A61B 8/5223* (2013.01); *A61B 5/02007* (2013.01); *A61B 5/027* (2013.01); *A61B 5/029* (2013.01); *A61B 5/0215* (2013.01); *A61B 5/0261* (2013.01); *A61B 5/7225* (2013.01); *A61B 5/7278* (2013.01); *A61B 2562/17* (2017.08); *A61B 2576/00* (2013.01)

(58) Field of Classification Search
CPC ... A61B 5/0295; A61B 5/7278; A61B 5/7225; A61B 5/029; A61B 5/0261; A61B 5/027; A61B 2576/00; A61B 5/02007; A61B 5/00

See application file for complete search history.

(56) References Cited

FOREIGN PATENT DOCUMENTS

| | | |
|---|---|---|
| JP | 2007-296354 A | 11/2007 |
| JP | 2012-501807 A | 1/2012 |
| JP | 2012-502773 A | 2/2012 |
| WO | WO 00/53081 A1 | 9/2000 |
| WO | WO 2010/030882 A1 | 3/2010 |
| WO | WO 2010/033971 A1 | 3/2010 |
| WO | WO 2011/090744 A2 | 7/2011 |

OTHER PUBLICATIONS

The Lipid, 2010 (month unknown), vol. 21, No. 1, pp. 58-64, (with English language summary).

\* cited by examiner

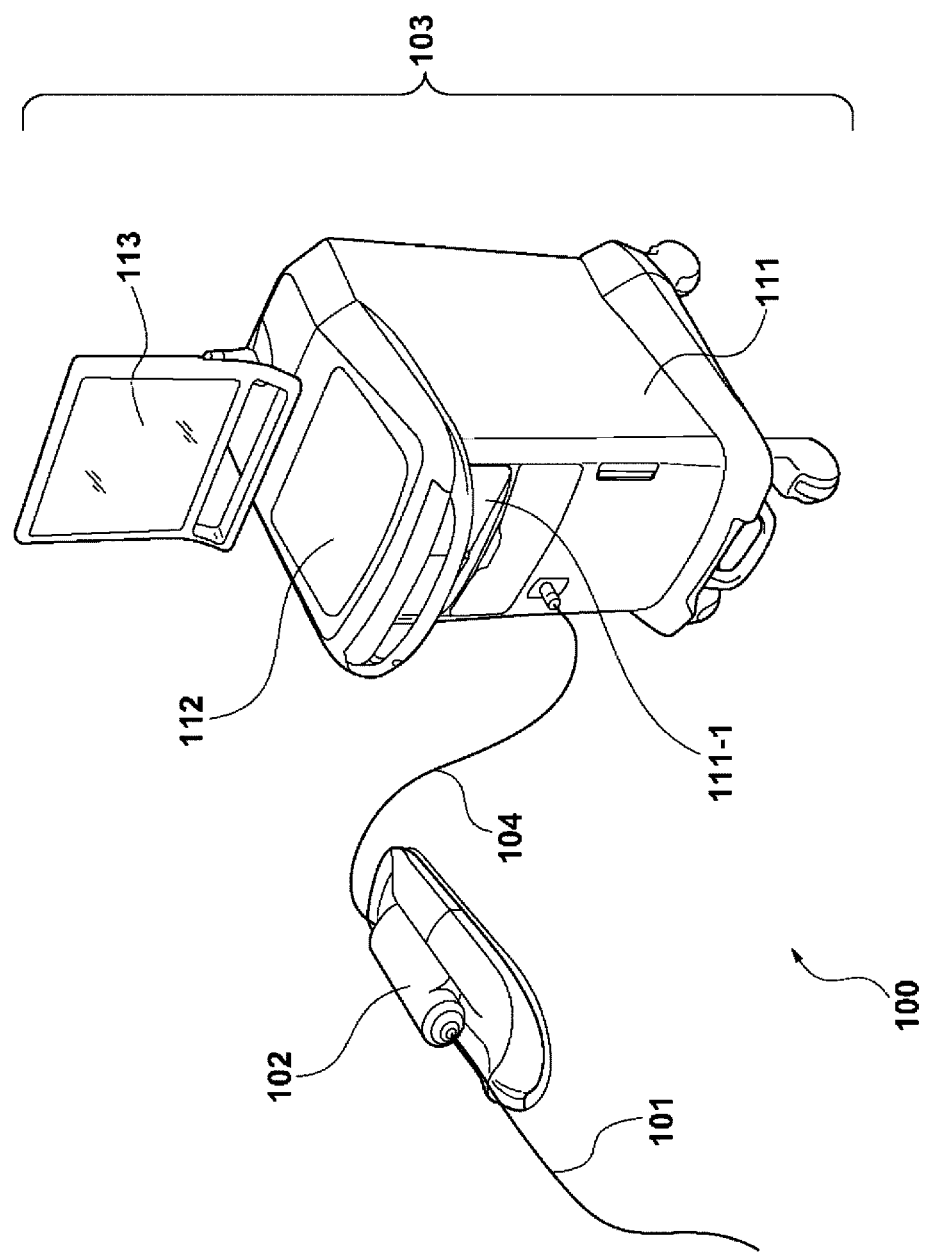
[FIG. 1]

[FIG. 2]
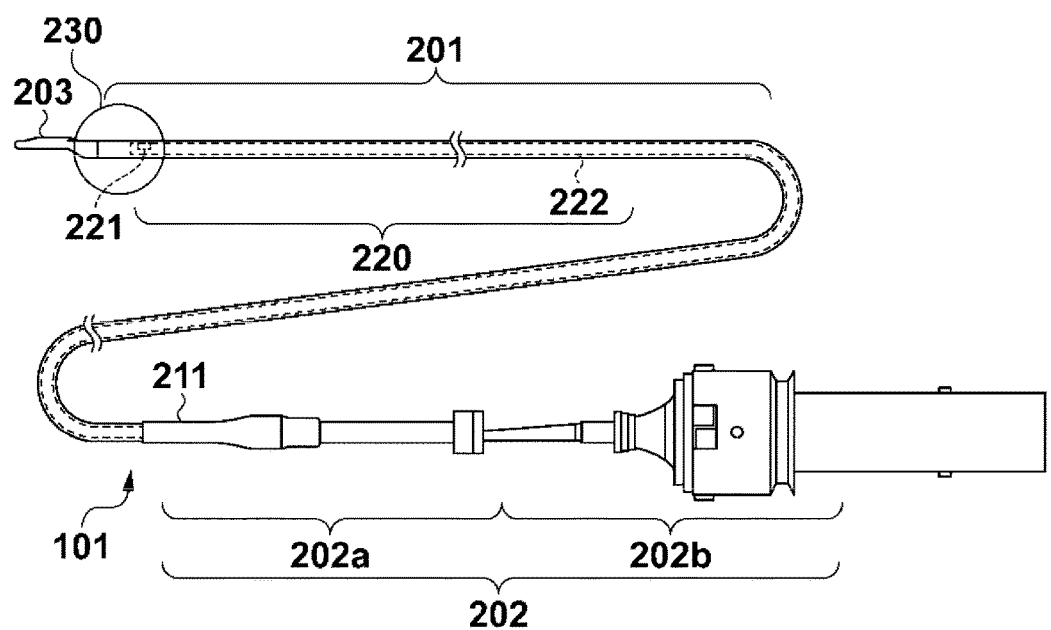

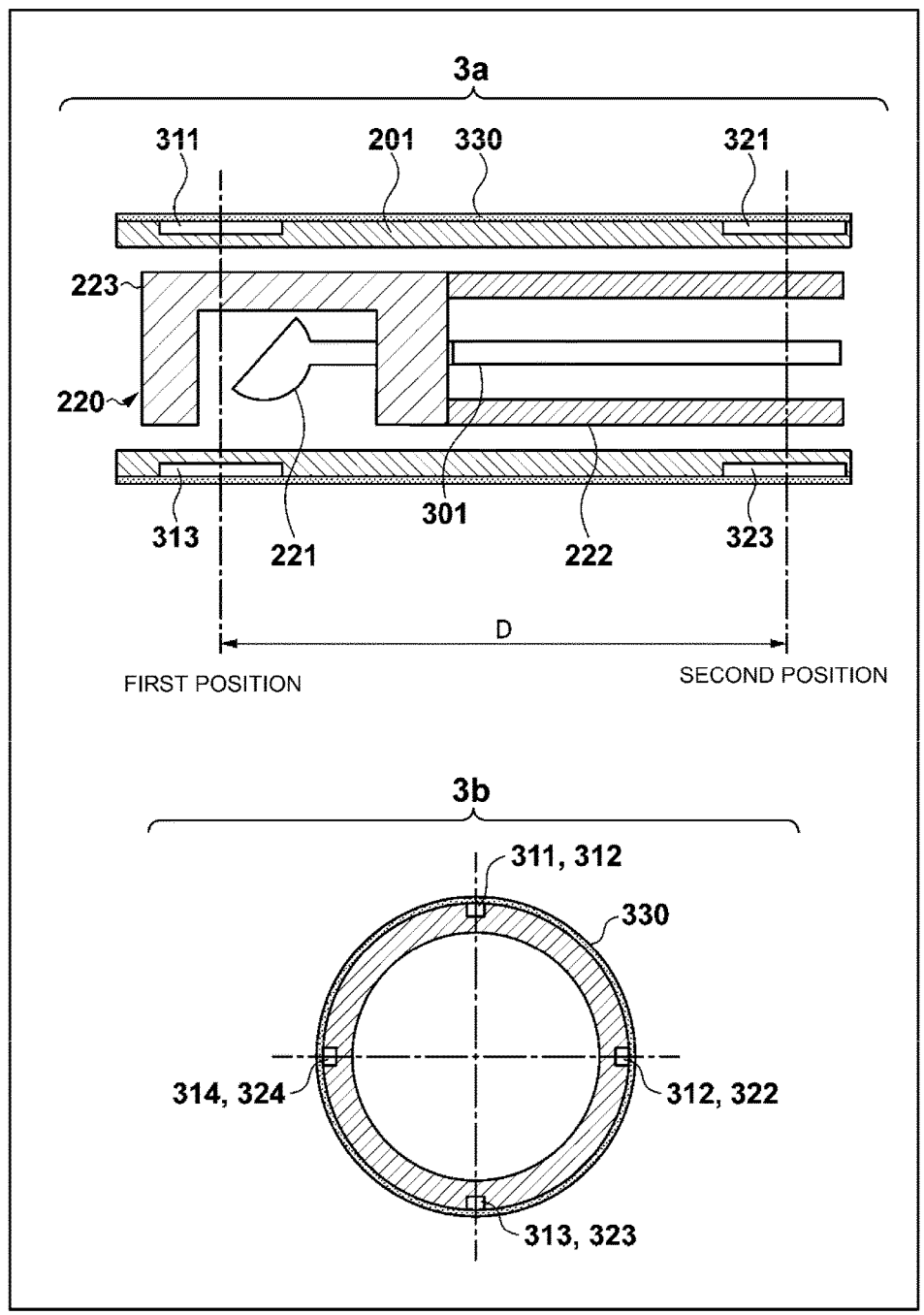

[FIG. 4]
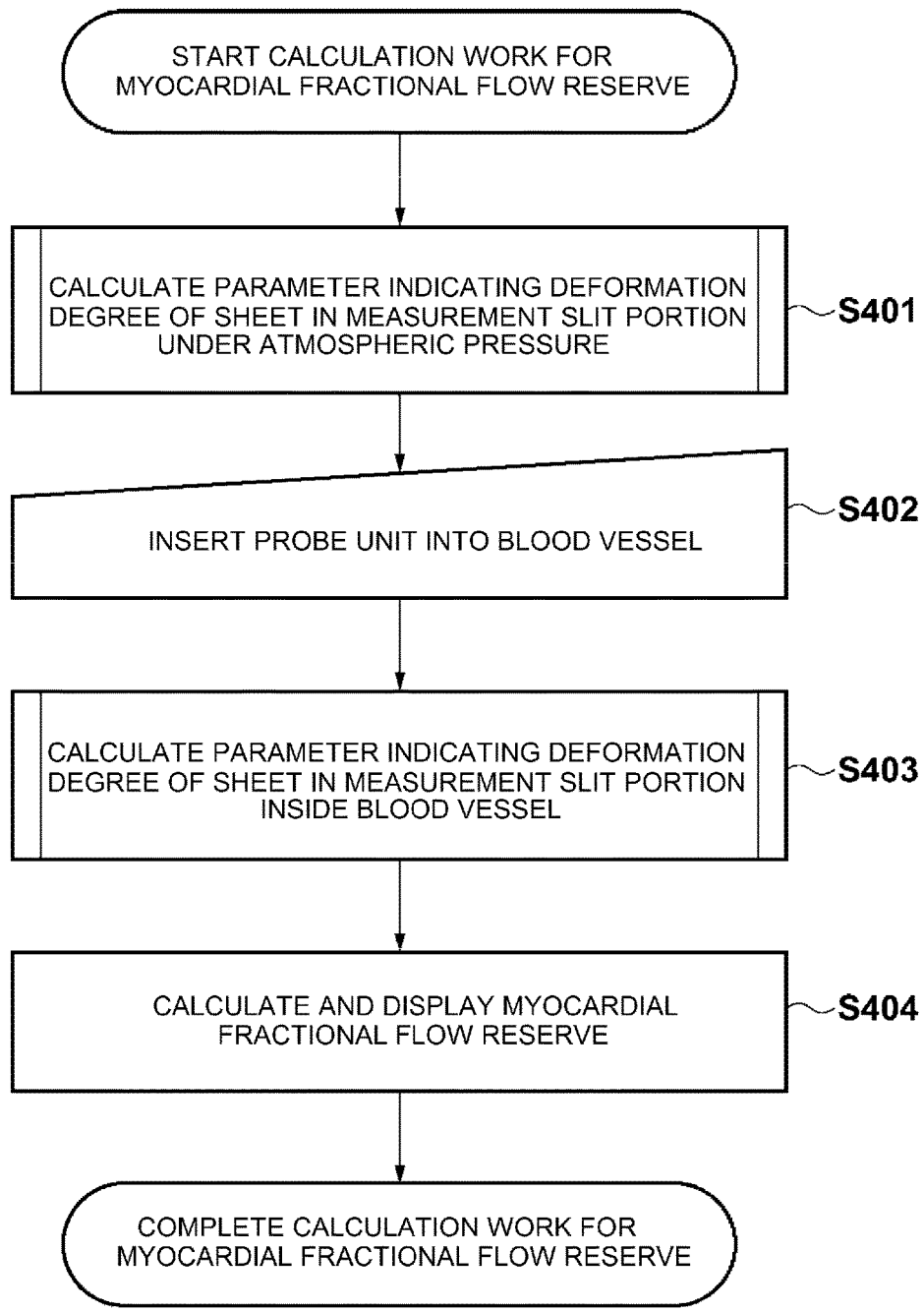

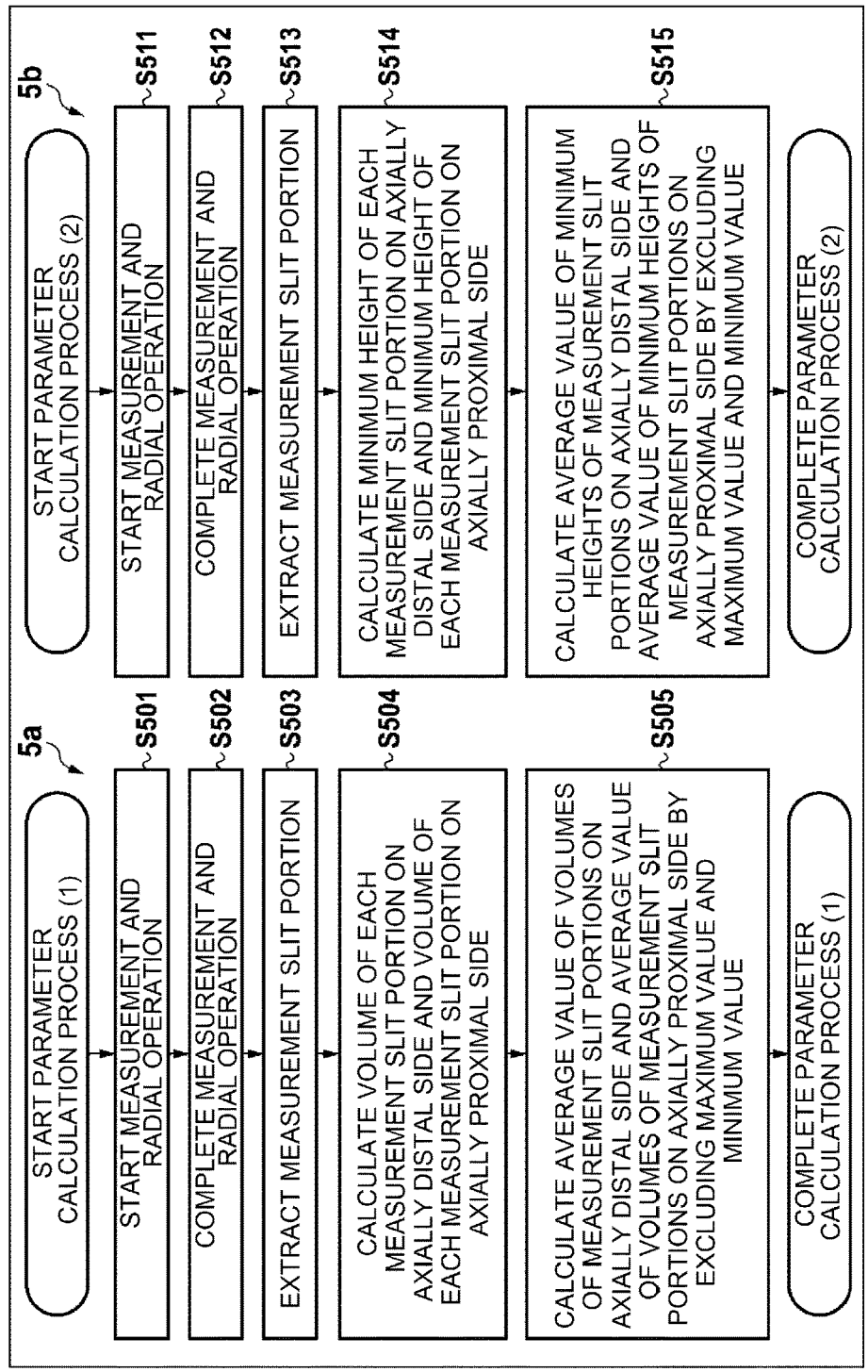
[FIG. 5A]

[FIG. 5B]
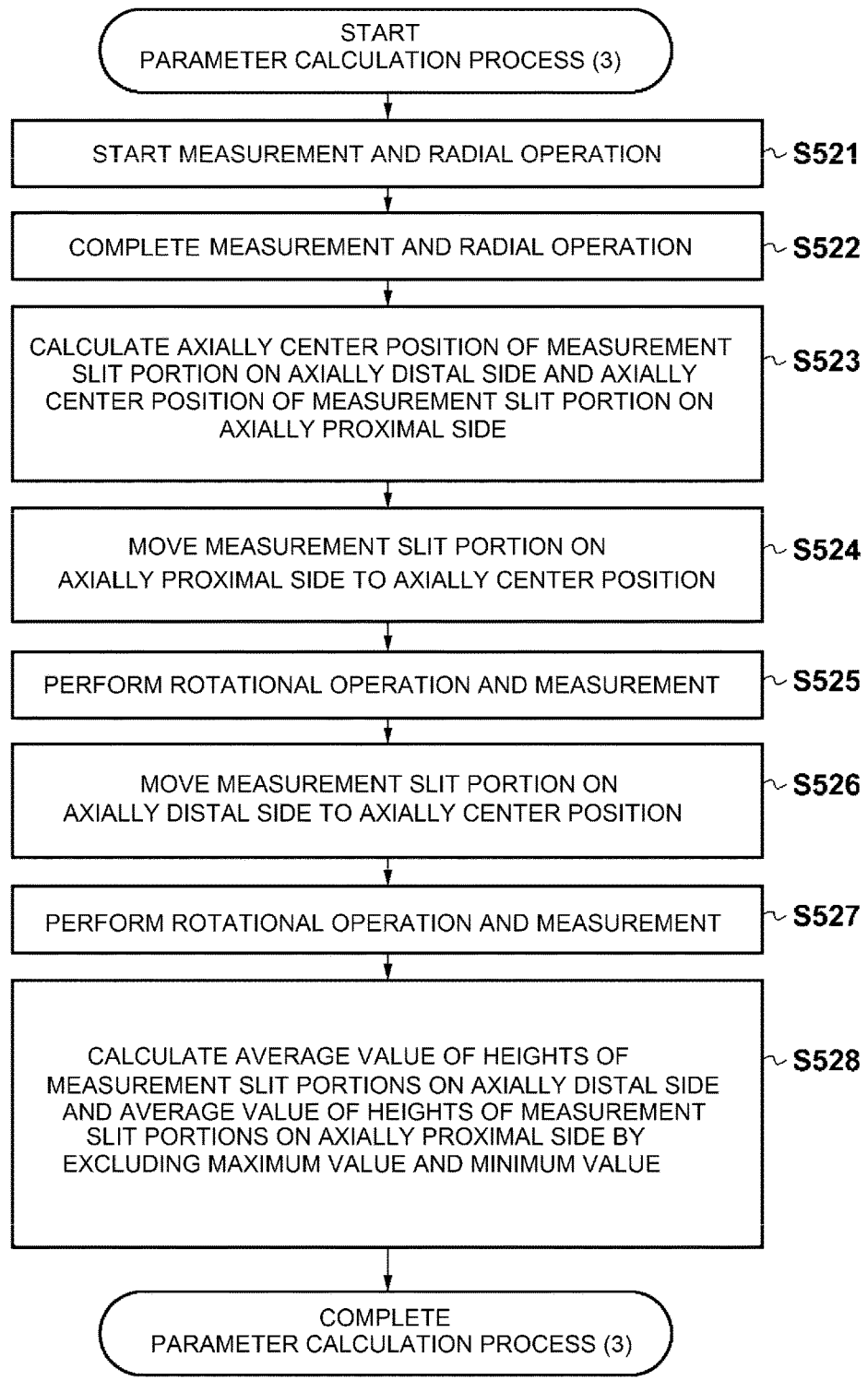

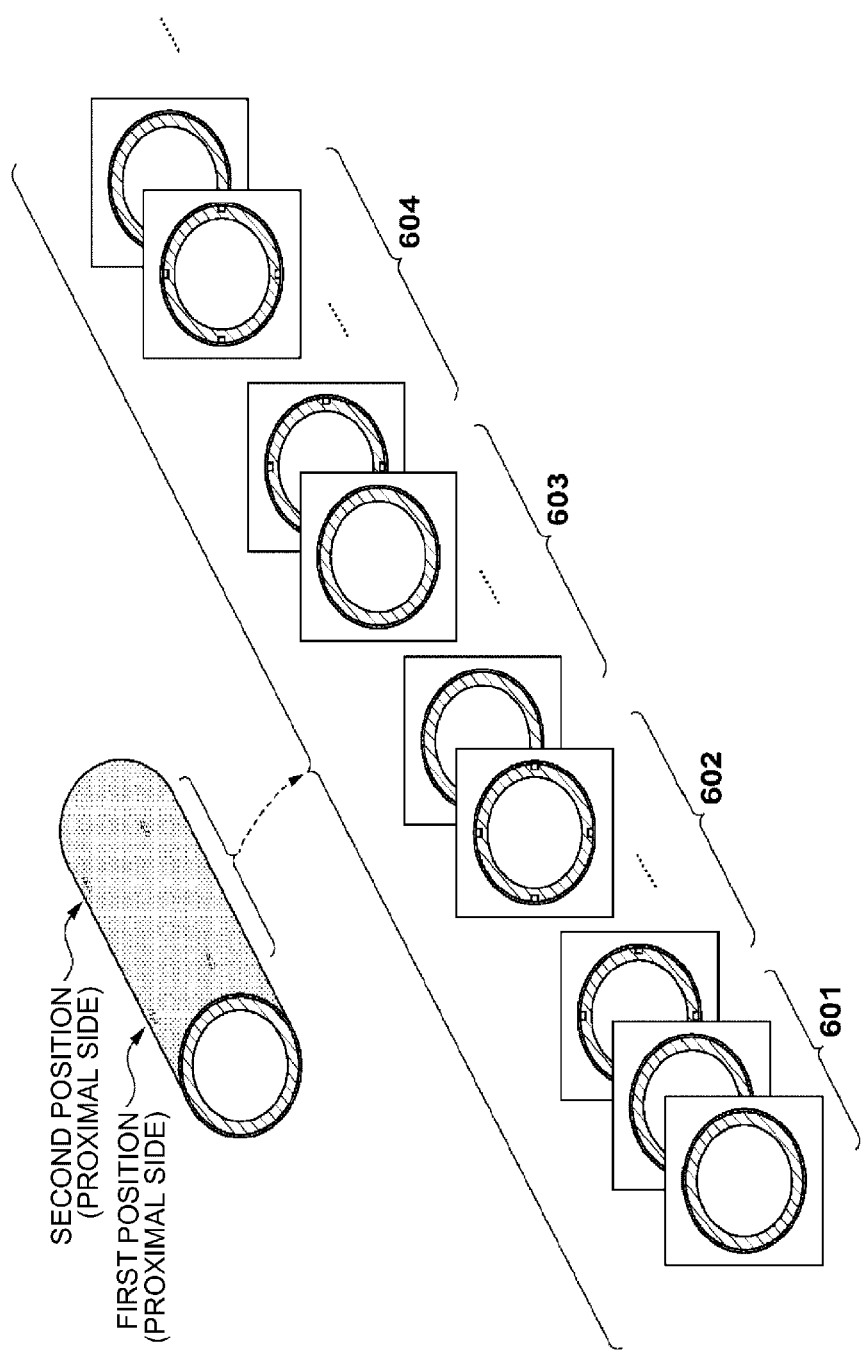
[FIG. 6A]

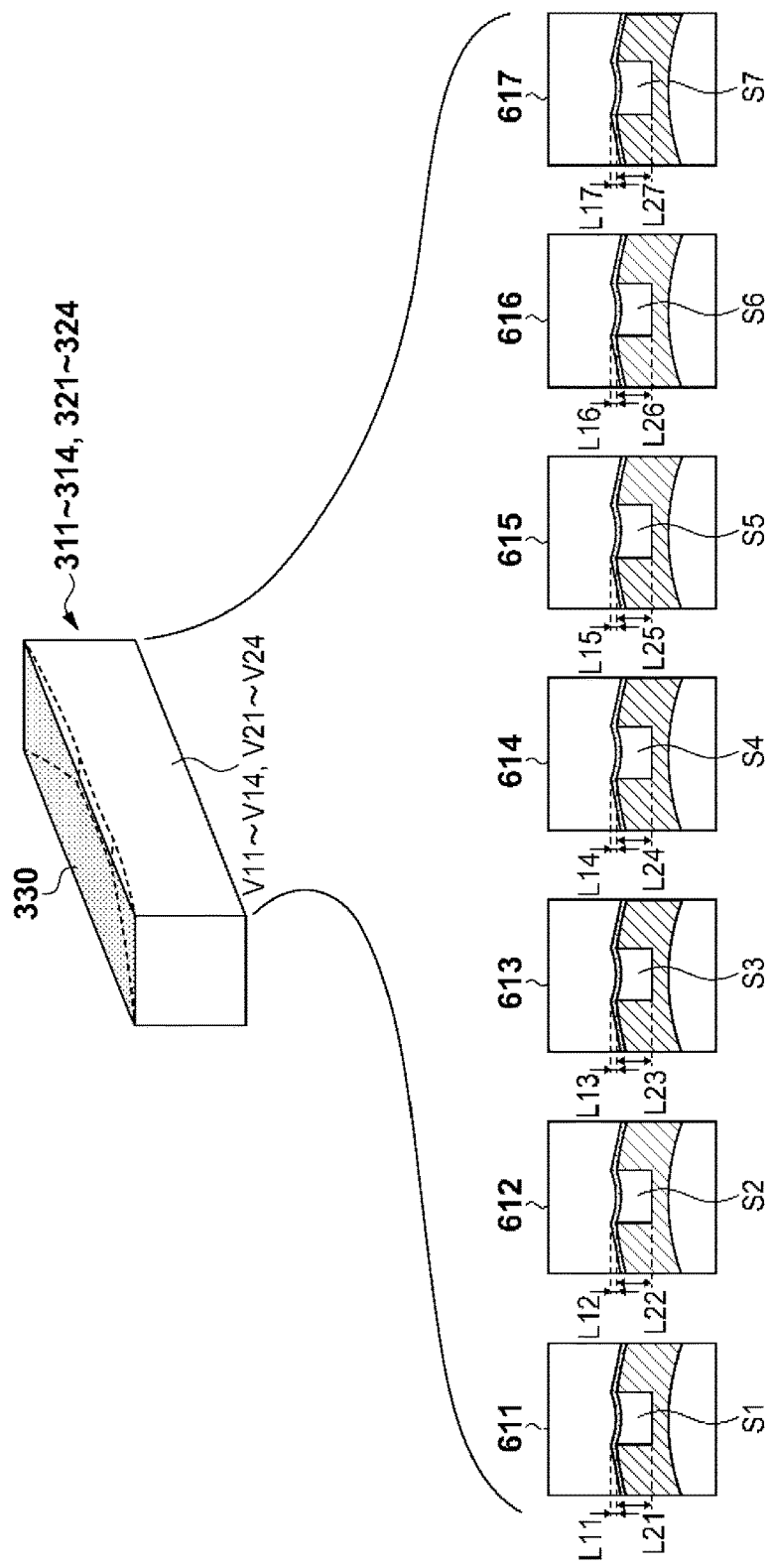

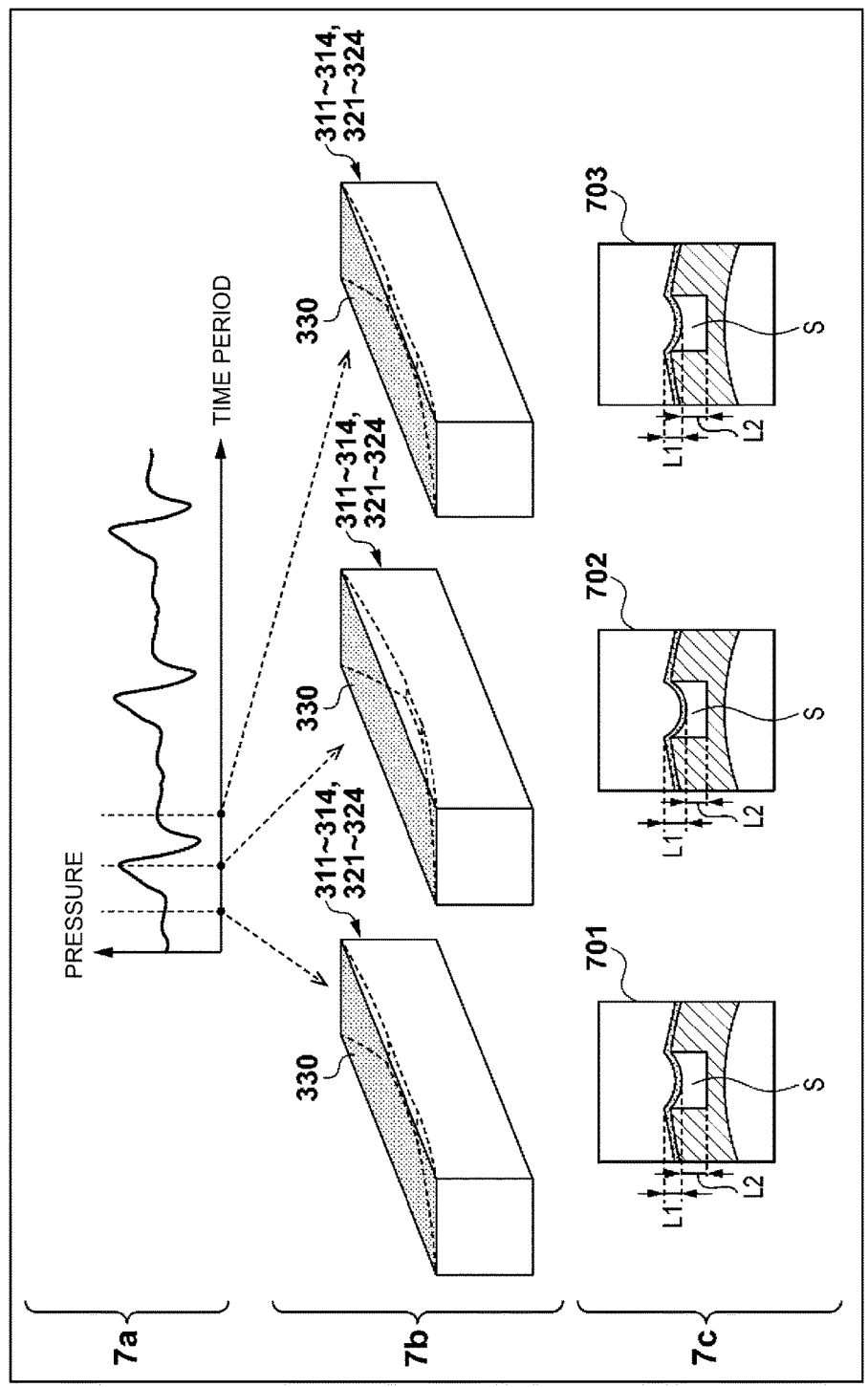

[FIG. 8]
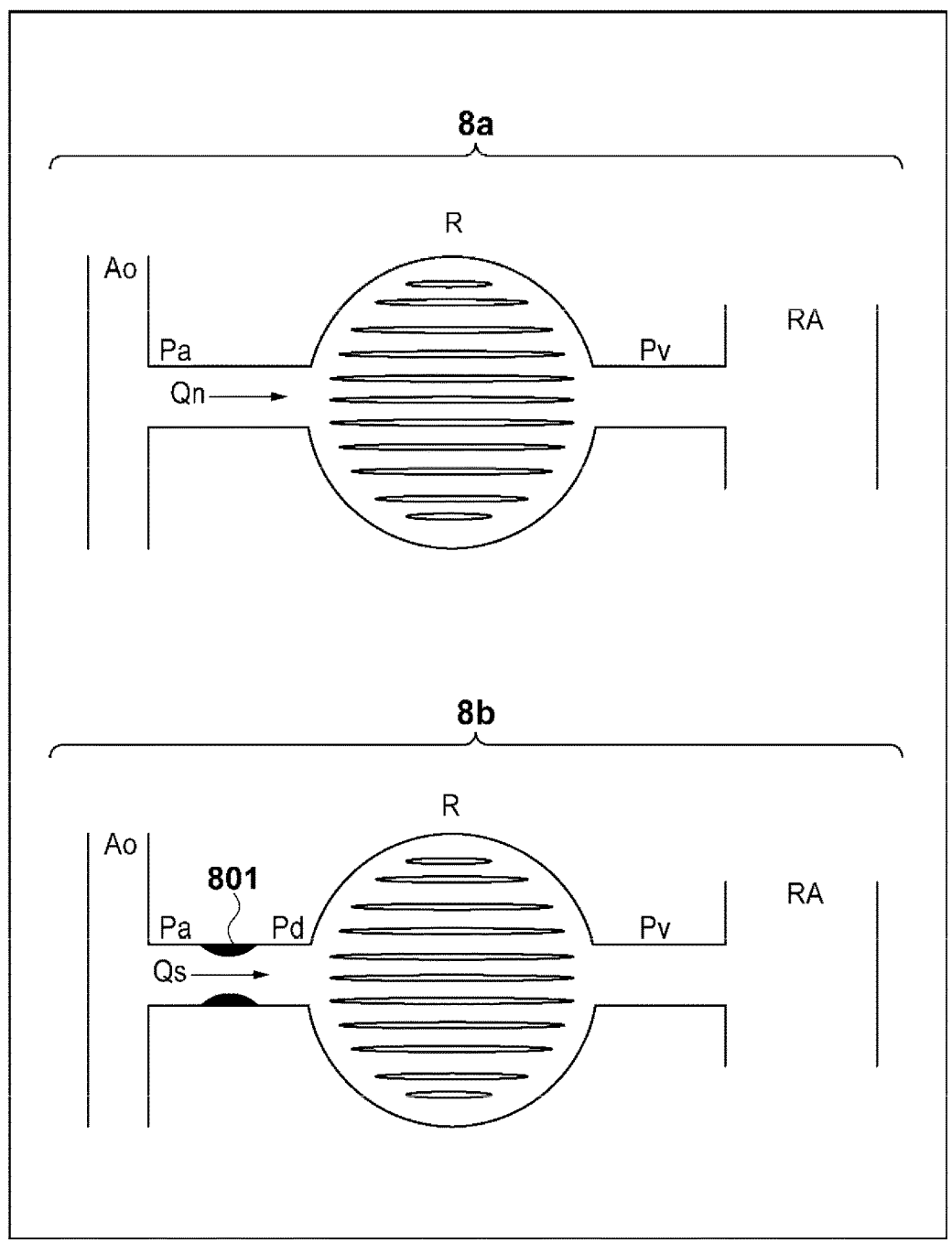
-- PRIOR ART --

[FIG. 9]
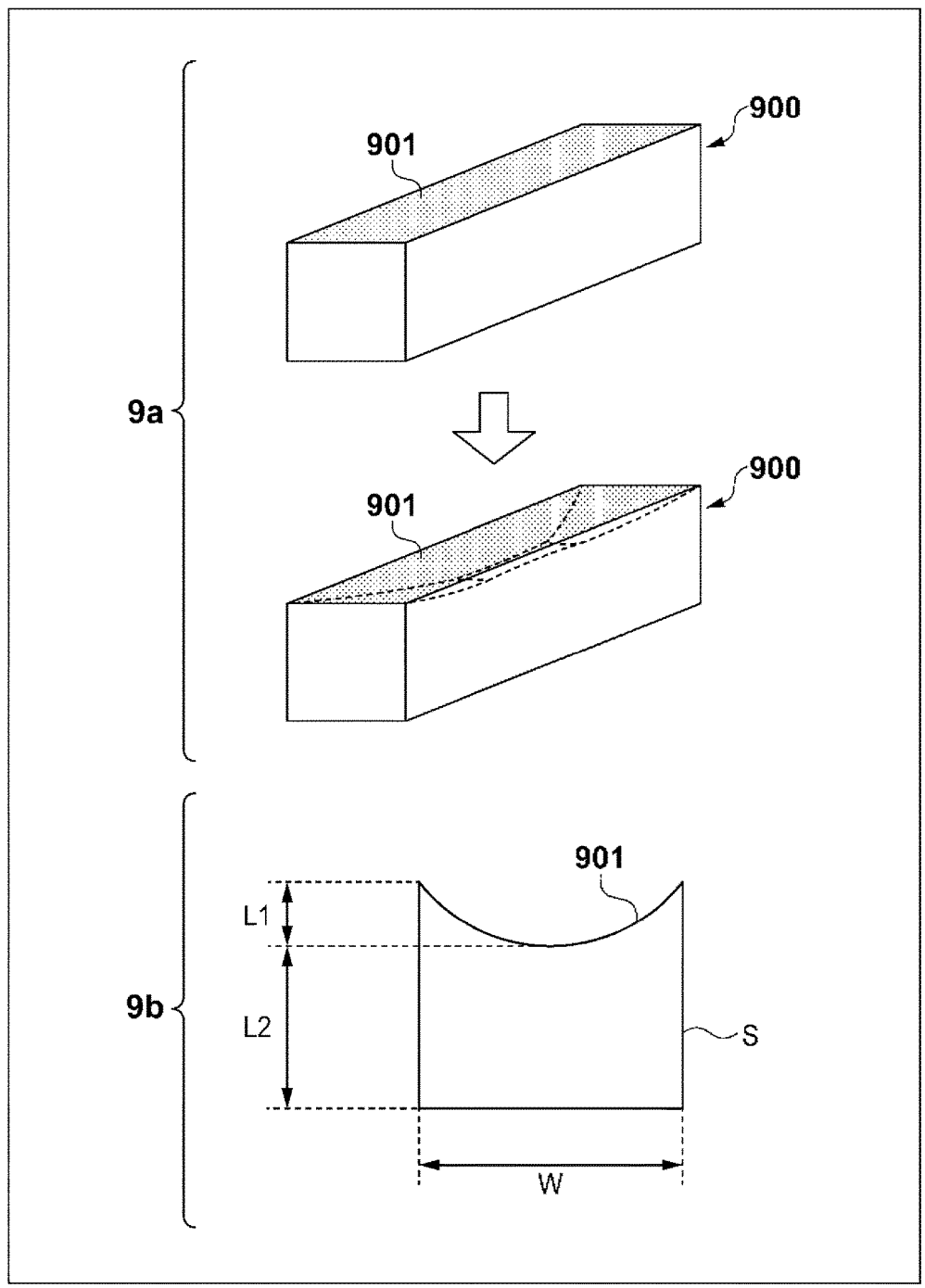

IMAGING APPARATUS FOR DIAGNOSIS AND PROBE

CROSS-REFERENCES TO RELATED APPLICATIONS

This application is a continuation of International Application No. PCT/JP2013/001866 filed on Mar. 19, 2013, and claims priority to Japanese Application No. 2012-076730 filed on Mar. 29, 2012, the entire content of both of which is incorporated herein by reference.

TECHNICAL FIELD

The disclosure here generally relates to an imaging apparatus for diagnosis and a probe.

BACKGROUND DISCUSSION

In the related art, an imaging apparatus for diagnosis has been widely used in order to perform diagnosis on arteriosclerosis, to perform preoperative diagnosis when endovascular therapy is performed by using a high-function catheter such as a balloon catheter or a stent, or to verify results after surgery.

The imaging apparatus for diagnosis includes an intravascular ultrasound (IVUS) device, an optical coherence tomography (OCT) device, and the like. The imaging apparatus for diagnosis is used to generate a tomographic image inside a blood vessel. In this manner, it is possible to perform anatomical diagnosis inside the blood vessel.

In recent years, it has been discovered that a therapeutic outcome is improved by using a physiological technique (method for evaluating presence or absence of actual ischemia or a degree of the ischemia) in addition to the above-described anatomical technique, as an intravascular diagnosis technique.

However, in order to perform intravascular diagnosis by using the physiological technique, it is necessary to use load echocardiography, stress electrocardiography, or stress myocardial scintigraphy. In general, it is difficult to use these devices concurrently with the anatomical technique.

In particular, during an emergency, or in a case of percutaneous coronary intervention, it becomes more difficult to perform these procedures concurrently with the anatomical technique.

On the other hand, in recent years, as an evaluation parameter in the physiological technique, a myocardial fractional flow reserve (FFR) has been focused on.

The myocardial fractional flow reserve is an indicator which indicates that blood flow flowing in a situation where a stenotic lesion is absent when a coronary artery is dilated to the maximum (during maximum coronary artery dilation) becomes a hindrance to some degree for the stenotic lesion. The myocardial fractional flow reserve can be calculated by measuring pressure at a proximal stenosis site and a pressure at a distal stenosis site during the maximum coronary artery dilation.

Therefore, it is possible to perform the physiological technique by arranging a pressure sensor inside a probe unit and measuring the pressures (for example, see Japanese Patent Application Publication No. 2003-525067, Japanese Patent Application Publication No. 2007-296354, Japanese Patent Application Publication No. 2012-501807, and Japanese Patent Application Publication No. 2012-502773. Also see, Takashi Akasaka: "Application of a Pressure Guide Wire with Thermography in the Assessment of Coronary Stenotic Lesions", Medical and Biological Engineering 43(1): 24-31, 2005).

Furthermore, if the pressure sensor is arranged inside a probe unit of the imaging apparatus for diagnosis so as to be compatible with a transmitting and receiving unit for generating a tomographic image, it is considered that a combined use of the anatomical technique and the physiological technique can be realized.

SUMMARY

However, if a configuration is employed in which in addition to the transmitting and receiving unit for generating a tomographic image, the pressure sensor is further arranged at a distal end position inside the probe unit of the imaging apparatus for diagnosis, there is a problem in that it is necessary not only to increase a diameter of the probe unit, but also to increase the cost.

For this reason, it is desirable to use the anatomical technique and the physiological technique in combination by employing a simpler configuration without using the pressure sensor.

The imaging apparatus for diagnosis disclosed here uses the anatomical technique and the physiological technique in combination by employing the simpler configuration in the imaging apparatus for diagnosis.

That is, there is provided an imaging apparatus for diagnosis including a probe unit that has a sheath and a transmitting and receiving unit inserted into the sheath and transmitting and receiving a signal, in which the transmitting and receiving unit is controlled so as to transmit and receive the signal while rotating inside the sheath in a circumferential direction or while rotating in the circumferential direction and moving in an axial direction, and in which deformation portions whose cross-sectional shape is deformed in response to an external pressure are respectively disposed at different positions of the sheath in the axial direction, first calculation means for calculating multiple parameters which indicate a deformation degree of the respective deformation portions disposed at the different positions in the axial direction, by using a tomographic image including the deformation portions, and second calculation means for calculating a value corresponding to a myocardial fractional flow reserve, based on the multiple parameters.

In an aspect of the disclosure here, a method of calculating a myocardial fractional flow reserve using an imaging apparatus for diagnosis includes calculating multiple parameters which indicate a deformation degree of the respective deformation portions disposed at the different positions in the axial direction, by using a tomographic image including the deformation portions, and calculating a value corresponding to the myocardial fractional flow reserve, based on the multiple parameters.

In the imaging apparatus for diagnosis, it is possible to measure a myocardial fractional flow reserve without providing a pressure sensor.

Other features and advantages of the disclosure here will become apparent from the following description made with reference to the accompanying drawings.

Note that, in the accompanying drawings, the same reference numerals are given to the same or similar configuring elements.

BRIEF DESCRIPTION OF DRAWINGS

The accompanying drawings are included in the specification, configure a part of the specification, illustrate embodiments of the imaging apparatus, and are used so as to describe principles of the imaging apparatus together with the description.

FIG. 1 is a view illustrating an external configuration of an imaging apparatus for diagnosis 100 according to an embodiment.

FIG. 2 is a view illustrating an overall configuration of a probe unit.

FIG. 3 is a view illustrating a detailed configuration of a distal end portion of a probe unit.

FIG. 4 is a flowchart illustrating calculation work flow of a myocardial fractional flow reserve.

FIG. 5A is a flowchart illustrating calculation process flow of a parameter indicating a deformation degree of a measurement slit portion.

FIG. 5B is a flowchart illustrating calculation process flow of a parameter indicating a deformation degree of a measurement slit portion.

FIG. 6A is a view illustrating an example of a generated tomographic image.

FIG. 6B is a view illustrating an example of an enlarged view of a generated tomographic image.

FIG. 7 is a view illustrating an example of a schematic view of a measurement slit portion which indicates a relationship with a pulse, and an enlarged view of a generated tomographic image.

FIG. 8 is a view for illustrating a myocardial fractional flow reserve.

FIG. 9 is a schematic view of a measurement slit portion.

DETAILED DESCRIPTION

Hereinafter, each embodiment will be described in detail with reference to the accompanying drawings.

1. Description of Myocardial Fractional Flow Reserve

First, an overview of a myocardial fractional flow reserve (FFR) which is an evaluation parameter used in a physiological technique will be described with reference to FIG. 8 cited from Takashi Akasaka's "Application of a Pressure Guide Wire with Thermography in the Assessment of Coronary Stenotic Lesions".

FIG. 8 is a schematic view for illustrating the myocardial fractional flow reserve (FFR).

As described above, the myocardial fractional flow reserve is an indicator which indicates that a blood flow flowing in a situation where stenotic lesion is absent during maximum coronary artery dilation becomes a hindrance to some degree for the stenotic lesion. 8a of FIG. 8 illustrates the blood flow flowing in a situation where the stenotic lesion is absent during the maximum coronary artery dilation (when an arteriole is dilated to the maximum by adding a drug thereto), and 8b of FIG. 8 illustrates the blood flow flowing in a situation where the stenotic lesion is present during the maximum coronary artery dilation.

In 8a of FIG. 8, Pa represents a pressure on an upstream side during the maximum coronary artery dilation, and Pv represents a coronary venous pressure.

Then, if resistance of a vascular system is assumed to be R, the maximum blood flow Qn flowing in the situation where the stenotic lesion is absent is expressed by Qn=(Pa−Pv)/R.

In contrast, in 8b of FIG. 8, Pa represents a pressure at a proximal site of a stenotic lesion 801, and Pd represents a pressure (equal to Pa in 8a of FIG. 8) at a distal site of the stenotic lesion 801.

In addition, Pv represents the coronary venous pressure.

Then, if the resistance of the vascular system during the maximum coronary artery dilation is assumed to be R, the maximum blood flow Qs flowing in the situation where the stenotic lesion is present is expressed by Qs=(Pd−Pv)/R.

Therefore, Qs/Qn which represents the myocardial fractional flow reserve (FFR) is expressed by the following equation.

$$Qs/Qn=(Pd-Pv)/(Pa-Pv) \quad \text{(Equation 1)}$$

Here, since the relation is expressed by Pd>>Pv and Pa>>Pv during the maximum coronary artery dilation, the myocardial fractional flow reserve (FFR) can be expressed by FFR≅Pd/Pa.

2. Calculation of Myocardial Fractional Flow Reserve Using Imaging Apparatus for Diagnosis Next, FIG. 9 which illustrates a calculation method of the myocardial fractional flow reserve using the imaging apparatus for diagnosis is a view for illustrating the calculation method of the myocardial fractional flow reserve using OCT. The reference numeral 900 is a measurement slit portion (deformation portion) in which a predetermined surface 901 is deformed in response to an intravascular pressure.

As described above, it is necessary to measure the intravascular pressures (Pd and Pa) in order to calculate the myocardial fractional flow reserve. However, if a configuration is employed in which a dedicated pressure sensor is arranged inside the probe unit in order to measure the intravascular pressures, there is a problem in that it is necessary not only to increase a diameter of the probe unit, but also to increase the cost.

Therefore, the imaging apparatus for diagnosis according to the present embodiment employs a configuration in which the measurement slit portion 900 which is deformed in response to the intravascular pressure is arranged in the probe unit, and in which a deformation degree of the surface 901 in the measurement slit portion 900 is quantitatively calculated based on a tomographic image, thereby measuring intravascular pressure.

The calculation of the myocardial fractional flow reserve may be sufficiently obtained if a ratio of the intravascular pressures (Pd/Pa) is calculated. The reason is because there is no need to calculate absolute pressure.

As illustrated in 9a of FIG. 9, the measurement slit portion 900 has a rectangular parallelepiped shape, and only the surface 901 is formed of a member having rigidity lower than that of the other surfaces of the measurement slit portion 900.

If the pressure is applied into the blood vessel, this configuration causes only the surface 901 to be deformed in a predetermined direction, and causes a cross-sectional shape of the measurement slit portion 900 to be deformed.

That is, with respect to the stenotic lesion, the measurement slit portions 900 are arranged so as to be respectively positioned on the axially distal side and the axially proximal side of the probe unit, and for example, a volume of the measurement slit portion 900 is calculated based on the tomographic image, as a parameter indicating a deformation degree in the respective measurement slit portions 900. According to this configuration, it is possible to calculate the myocardial fractional flow reserve.

Specifically, the following relational equation is satisfied if it is assumed that a volume of one measurement slit portion (measurement slit portion located on the axially distal side of the probe unit with respect to the stenotic lesion, when being inserted into the blood vessel) under atmospheric pressure $P_0$ is $V_{f0}$, a volume of the other measurement slit portion (measurement slit portion located on the axially proximal side of the probe unit with respect to the stenotic lesion, when being inserted into the blood vessel) is $V_{b0}$, and further, a volume of the measurement slit portion on the axially distal side in a state of being actually inserted into the blood vessel is $V_{f1}$, a volume of the measurement slit portion on the axially proximal side in a state of being actually inserted into the blood vessel is $V_{b1}$, a pressure applied to the measurement slit portion on the axially distal side inside the blood vessel is $P_f$, and a pressure applied to the measurement slit portion on the axially proximal side inside the blood vessel is $P_b$.

$$P_f \times V_{f1} = P_0 \times V_{f0} \qquad \text{(Equation 2)}$$

$$P_b \times V_{b1} = P_D \times V_{b0} \qquad \text{(Equation 3)}$$

Therefore, the myocardial fractional flow reserve (FFR) is expressed by the following equation.

$$FFR = P_b/P_f = \{(P_0 \times V_{b0})/V_{b1}\}/\{(P_0 \times V_{f0})/V_{f1}\} = (V_{b0} \times V_{f1})/(V_{b1} \times V_{f0}) \qquad \text{(Equation 4)}$$

That is, it is possible to calculate the myocardial fractional flow reserve by using the tomographic image generated by the imaging apparatus for diagnosis and by respectively calculating the volume of the measurement slit portion on the axially distal side under the atmosphere and the volume inside the blood vessel, and the volume of the measurement slit portion on the axially proximal side under the atmosphere and the volume inside the blood vessel.

Note that, as apparent from the above description, the imaging apparatus for diagnosis according to the present embodiment calculates the myocardial fractional flow reserve by capturing a change in the pressure as the deformation degree in the measurement slit portion.

Therefore, if a parameter indicates the deformation degree in the measurement slit portion, the parameter is not limited to the above-described volume of the measurement slit portion. For example, an area S of a specific cross section (cross section at a position in which the surface 901 is deformed the most) of the measurement slit portion may be used as the parameter (refer to 9b of FIG. 9).

Alternatively, a distortion amount (L1/W) of the surface 901 in the specific cross section (cross section at a position in which the surface 901 is deformed the most) of the measurement slit portion, or a height (L2) from a bottom surface of the surface 901 may be used as the parameter (refer to 9b of FIG. 9).

3. External Configuration of Imaging Apparatus for Diagnosis

Next, an external configuration of the imaging apparatus for diagnosis according to the present embodiment which calculates the above-described myocardial fractional flow reserve will be described.

FIG. 1 is a view illustrating the external configuration of an imaging apparatus for diagnosis (here, to be described as OCT) 100 according to an embodiment.

As illustrated in FIG. 1, the imaging apparatus for diagnosis 100 includes a probe unit (probe) 101, a scanner and pullback unit (motor drive unit) 102, and an operation control apparatus 103. The scanner and pullback unit 102 and the operation control apparatus 103 are connected to each other by a signal line 104.

The probe unit 101 is directly inserted into a body lumen such as the blood vessel, and continuously transmits transmitted measurement light toward biological tissues. An imaging core which includes a transmitting and receiving unit continuously receiving reflected light from the biological tissues in a distal end of the imaging core is internally inserted into a catheter sheath, thereby using the imaging core to measure a state of the biological tissues.

The scanner and pullback unit 102 is configured so that the probe unit 101 is detachably attached to it. A radial operation (operation in the axial direction and operation in the rotation direction inside the body lumen) of the imaging core internally inserted into the probe unit 101 is realized by driving a built-in motor.

In addition, the scanner and pullback unit 102 acquires the reflected light received by the transmitting and receiving unit, and transmits the acquired reflected light to the operation control apparatus 103 via the signal line 104.

When the measurement is performed, the operation control apparatus 103 includes a function for inputting various setting values and a function for displaying a measurement result as the tomographic image of the biological tissues.

In the operation control apparatus 103, the reference numeral 111 represents a main body control unit. The main body control unit 111 generates interference light data by causing the reflected light obtained by the measurement to interfere with reference light obtained by splitting the measurement light, and performs processing on line data (data of a line in a radiating direction in the tomographic image) generated based on the interference light data, thereby constructing multiple tomographic images inside the body lumen in the axial direction.

In addition, the myocardial fractional flow reserve is calculated based on the constructed tomographic images.

The main body control unit 111 represents an example of an extraction means (to be described later) for performing extraction work of the image and represents an example of calculation means (first calculation means, second calculation means, and third calculation means) for performing calculation work of the parameter.

The reference numeral 111-1 represents a printer & DVD recorder, which prints a processing result in the main body control unit 111 or stores the processing result as data.

The reference numeral 112 represents an operation panel. A user inputs various setting values and instructions via the operation panel 112.

The reference numeral 113 represents an LCD monitor serving as a display apparatus. The LCD monitor displays the multiple tomographic images of the biological tissues which are constructed in the main body control unit 111.

4. Configuration of Probe Unit

Next, a configuration of the probe unit 101 will be described with reference to FIG. 2.

As illustrated in FIG. 2, the probe unit 101 is configured to have an elongated catheter sheath 201 to be inserted into the body lumen such as the blood vessel, and a connector 202 which is not inserted into the body lumen such as the blood vessel and is arranged on a user's hand-side for the user's operation.

A tube for a guidewire lumen 203 which configures a guide wire lumen is disposed in a distal end of the catheter sheath 201. That is, the distal end of the catheter sheath 201 includes a tube 203 possessing a guide wire lumen configured to receive a guide wire.

The catheter sheath 201 forms a lumen which is continuous from a connection portion with the tube for the guidewire lumen 203 to a connection portion with the connector 202.

The lumen of the catheter sheath 201 internally includes an optical transmitting and receiving unit 221 for transmitting and receiving light and an optical fiber cable. An imaging core 220 including a coil-shaped drive shaft 222 which transmits a rotational drive force for rotating both of these is inserted into the catheter sheath 201 over substantially the entire length of the catheter sheath 201.

The connector 202 includes a sheath connector 202a configured to be integrated with the proximal end of the catheter sheath 201 and a drive shaft connector 202b configured to rotatably fix the drive shaft 222, in the proximal end of the drive shaft 222.

An anti-kink protector 211 is disposed in a boundary portion between the sheath connector 202a and the catheter sheath 201.

This maintains predetermined rigidity. Accordingly, it is possible to prevent bending (kinking) which may occur due to an abrupt change in physical properties.

The scanner and pullback unit 102 is detachably attached to the proximal end of the drive shaft connector 202b.

5. Detailed Configuration of Distal End Portion of Probe Unit

Next, a detailed configuration of a distal end portion (refer to 230 in FIG. 2) of the probe unit 101 will be described with reference to FIG. 3.

FIG. 3 is a view illustrating the detailed configuration of the distal end portion of the probe unit 101. Respectively, 3a of FIG. 3 illustrates a cross-sectional view when the distal end portion of the probe unit 101 is viewed from the side surface, and 3b of FIG. 3 illustrates a cross-sectional view at a first position and a second position in 3a of FIG. 3 when the distal end portion of the probe unit 101 is viewed from the distal side (note that, in 3b of FIG. 3, the imaging core 220 is omitted for convenience of description).

As illustrated in 3a of FIG. 3, a sideways radiation-type ball lens (optical transmitting and receiving unit) 221 is arranged inside a housing 223. An optical fiber cable 301 configured to have a cladding portion and a core portion is arranged inside the drive shaft 222.

Note that light transmitted from the optical transmitting and receiving unit 221 is radiated to the biological tissues inside the body lumen through the catheter sheath 201.

In addition, multiple measurement slit portions (311 to 314 and 321 to 324) are disposed in the catheter sheath 201.

The measurement slit portions (311 to 314 and 321 to 324) are configured to have multiple grooves disposed on an outer surface of the sheath 201, and to have a uniform width parallel to the circumferential direction of the probe unit 101 and a predetermined length parallel to the axial direction. The measurement slit portions (311 to 314 and 321 to 324) are disposed at a first position in the axial direction and a second position which is apart from the first position by a predetermined distance D.

All the respective measurement slit portions have the same width, length, and arrangement angle.

Furthermore, an outer circumferential surface of the catheter sheath 201 is covered with a flexible sheet (cover) 330 which is deformed in response to a pressure change in the external environment.

The measurement slit portions are disposed at the first position and the second position in the axial direction as described above, so as to capture deformation of the sheet 330 in the measurement slit portion located on the axially distal side of the probe unit 101 and deformation of the sheet 330 in the measurement slit portion located on the axially proximal side, with respect to the stenotic lesion.

That is, the probe unit 101 is arranged inside the blood vessel so that the stenotic lesion is located between the first position and the second position. In this manner, it is possible to capture the deformation of the sheet 330 which is caused by the blood pressure on further the distal side than the stenotic lesion, and the deformation of the sheet 330 which is caused by the blood pressure further on the proximal side than the stenotic lesion.

Note that, as illustrated in 3b of FIG. 3, in the present embodiment, four measurement slit portions (311 to 314 and 321 to 324) are respectively disposed at the first position and the second position in the circumferential direction of the catheter sheath 201.

The multiple measurement slit portions are configured to be respectively disposed at the first position and the second position in the circumferential direction in this manner, so as to more accurately calculate the myocardial fractional flow reserve (FFR) by respectively analyzing a deformation degree of the sheet 330 in the multiple measurement slit portions.

6. Flow of Calculation Work for Myocardial Fractional Flow Reserve

Next, flow of calculation work for the myocardial fractional flow reserve which uses the imaging apparatus for diagnosis 100 will be described with reference to FIG. 4.

FIG. 4 is a flowchart illustrating the flow of calculation work for the myocardial fractional flow reserve.

As illustrated in FIG. 4, in Step S401, under atmospheric pressure (that is, in a state before the probe unit 101 is inserted into the blood vessel of a subject), parameters ($V_{b0}$, $V_{f0}$) indicating the deformation degree of the sheet 330 in the respective measurement slit portions at the first and second positions are calculated.

Specifically, in a range including the first and second positions, the measurement is performed while the imaging core 220 is caused to perform a radial operation. In this manner, the parameters indicating the deformation degree of the sheet 330 in the respective measurement slit portions are measured.

Note that, details of a calculation process for the parameters indicating the deformation degree in the measurement slit portions will be described later with reference to FIGS. 5A, 5B, 6A, and 6B.

In Step S402, the probe unit 101 is inserted into the blood vessel of the subject.

Furthermore, in Step S403, in the blood vessel of the subject, the measurement slit portion at the first position is arranged to be located on the axially distal side of the probe unit 101 with respect to the stenotic lesion to be diagnosed, and the measurement slit portion at the second position is arranged to be located on the axially proximal side of the probe unit 101 with respect to the stenotic lesion to be diagnosed.

In order to facilitate this work, an X-ray contrast marker (X-ray opaque portion) for visually checking the first position and the second position during an X-ray contrast inspection may be disposed in the sheath 201.

Thereafter, the parameters indicating the deformation degree of the sheet 330 in the respective measurement slit portions at the first position and the second position are calculated.

Specifically, in a range including the first and second positions, parameters ($V_{f1}$, $V_{b1}$) indicating the deformation degree of the sheet 330 in the respective measurement slit portions are measured by causing the imaging core 220 to perform the radial operation.

Note that, a calculation method for the parameters indicating the deformation degree in the measurement slit portions will be described later with reference to FIGS. 5A, 5B, 6A, and 6B.

In Step S404, the myocardial fractional flow reserve is calculated by using the parameters indicating the deformation degree in the respective measurement slit portions which are calculated in Step S401 and Step S403, and then is displayed on the LCD monitor 113.

7. Parameter Calculation Process

Next, details of a process for calculating the parameters (hereinafter, referred to as a parameter calculation process) indicating the deformation degree of the sheet 330 in the measurement slit portion, which is illustrated in Steps S401 and S403 in FIG. 4, will be described with reference to FIGS. 5A, 5B, 6A, and 6B.

FIGS. 5A and 5B are flowcharts illustrating flow of parameter calculation processes (three types of process), and FIGS. 6A and 6B are views illustrating an example of a tomographic image generated during the parameter calculation processes and enlarged views of the tomographic image.

7.1 Case of Parameter Calculation Process (1)

As illustrated in 5a of FIG. 5A, in Step S501, the imaging apparatus for diagnosis 100 starts to transmit and receive light, starts the radial operation, and starts to generate the tomographic image of the catheter sheath 201.

If scanning of the first position and the second position is completed by the radial operation, in Step S502, the light transmitting and the light receiving are completed, and the radial operation is completed.

FIG. 6A illustrates an example of the tomographic image generated by performing the measurement in Steps S501 and S502.

As illustrated in FIG. 6A, the tomographic image of the catheter sheath 201 which is captured immediately after the measurement is started does not include the measurement slit portion (refer to 601). However, if the catheter sheath 201 reaches the measurement slit portion at the first position, the measurement slit portion appears on the tomographic image of the catheter sheath 201 (refer to 602).

If the measurement progresses further, the measurement slit portion is no longer included again (refer to 603). If the catheter sheath 201 reaches the measurement slit portion at the second position, the measurement slit portion appears again (refer to 604).

If the radial operation is performed so that the measurement slit portions at the first position and the second position as described above are included, the tomographic image including the measurement slit portion and the tomographic image without including the measurement slit portion are mixed with each other.

Therefore, in Step S503, extraction means (main body control unit 111) extracts only the tomographic image including the measurement slit portion.

Furthermore, in Step S504, the tomographic image extracted in Step S503 is classified into a tomographic image (602) including the measurement slit portion at the first position and a tomographic image (604) including the measurement slit portion at the second position.

Furthermore, first calculation means (main body control unit 111) calculates respective volumes for the measurement slit portions at the first position (in the present embodiment, the measurement slit portions 311 to 314) and the measurement slit portions at the second position (in the present embodiment, the measurement slit portions 321 to 324).

FIG. 6B illustrates an example of enlarged views of the tomographic image extracted in Step S503.

As illustrated in FIG. 6B, cross-sectional areas S1 to S7 of the measurement slit portions included in respective tomographic images 611 to 617 are calculated, and these are integrated in the axial direction of the probe unit 101. In this manner, it is possible to calculate the volume of the measurement slit portion.

In Step S504, volumes V11 to V14 are calculated with regard to the respective measurement slit portions 311 to 314 at the first position, and volumes V21 to V24 are calculated with regard to the respective measurement slit portions 321 to 324 at the second position.

In Step S505, from among the volumes V11 to V14 of the measurement slit portions 311 to 314 at the first position, the maximum value and the minimum value are excluded without being employed, and an average value of the volumes is calculated by employing the remaining two volumes (that is, the average value is calculated by employing only the volumes of partial measurement slit portions).

Similarly, from among the volumes V21 to V24 of the measurement slit portions 321 to 324 at the second position, the maximum value and the minimum value are excluded without being employed, and an average value of the volumes is calculated by employing the remaining two volumes.

These processes are performed in Steps S401 and S403. In this manner, it is possible to calculate parameters ($V_{b0}$, $V_{f1}$, $V_{b1}$, and $V_{f0}$) illustrating the deformation degrees in the measurement slit portions which are required for second calculation means (main body control unit 111) to calculate the myocardial fractional flow reserve (FFR).

7.2 Case of Parameter Calculation Process (2)

Next, a parameter calculation process illustrated in 5b of FIG. 5A will be described.

Note that, processes from Steps S511 to S513 in 5b of FIG. 5A are the same as processes from Steps S501 to S503 in 5a of FIG. 5A. Therefore, description of these steps will not be repeated.

In Step S514, the tomographic image extracted in Step S513 is classified into a tomographic image (602) including the measurement slit portion at the first position and a tomographic image (604) including the measurement slit portion at the second position.

Furthermore, heights (L2) of the sheet 330 respectively are calculated with regard to the measurement slit portions at the first position (in the present embodiment, the measurement slit portions 311 to 314) and the measurement slit portions at the second position (in the present embodiment, the measurement slit portions 321 to 324).

FIG. 6B illustrates an example of enlarged views of the tomographic image extracted in Step S513.

As illustrated in FIG. 6B, heights L21 to L27 of the sheets 330 are calculated with regard to the respective measurement slit portions included in the respective tomographic images 611 to 617.

Then, the tomographic image in which the height of the sheet 330 is the lowest (L24) is selected from the respective tomographic images 611 to 617.

In this manner, the tomographic image in which the height of the sheet 330 is the lowest (normally, a tomographic image at an axially center position of the measurement slit portions) for the respective measurement slit portions can be selected.

These processes are performed in the measurement slit portions 311 to 314 at the first position. In this manner, four tomographic images are selected from the first position.

Similarly, four tomographic images are also selected from the measurement slit portions 321 to 324 at the second position.

In Step S515, with regard to the measurement slit portions 311 to 314 at the first position, the maximum value and the minimum value are excluded from the height (L24) of the sheet 330 in the four tomographic images selected in Step S514, and the average value with regard to the height (L24) of the remaining two sheets 330 is calculated.

Similarly, with regard to the measurement slit portions 321 to 324 at the second position, the maximum value and the minimum value from among the height (L24) of the sheet 330 in the four tomographic images selected in Step S514 are excluded, and the average value with regard to the height (L24) of the remaining two sheets 330 is calculated.

These processes are performed in Steps S401 and S403. In this manner, it is possible to calculate parameters ($L24_{b0}$, $L24_{f1}$, $L24_{b1}$, and $L24_{f0}$) illustrating the deformation degrees in the measurement slit portions which are required for calculating the myocardial fractional flow reserve (FFR).

Note that, herein, a configuration for obtaining the height (L24) from a bottom surface of the measurement slit portion to the sheet 330 is adopted. However, the imaging apparatus for diagnosis is not limited in this way, and the same process may be performed for a cross-sectional area (S4) or a distortion amount of the sheet 330 (L14/W).

7.3 Case of Parameter Calculation Process (3)

Next, a parameter calculation process illustrated in FIG. 5B will be described.

Note that, processes from Steps S521 to S522 in FIG. 5B are the same as processes from Steps S501 to S502 in 5a of FIG. 5A. Therefore, description of these steps will be omitted herein.

In Step S523, based on the tomographic image generated in Steps S521 and S522, third calculation means (main body control unit 111) calculates the axially center position of the measurement slit portions at the first position.

Similarly, the third calculation means calculates the axially center position of the measurement slit portions at the second position.

In Step S524, the imaging core 220 is moved so that the optical transmitting and receiving unit 221 is located at the axially center position of the measurement slit portions at the second position which is calculated in Step S523.

In Step S525, the light transmitting and the light receiving are started at the axially center position of the measurement slit portions at the second position, a rotary operation is started, and the tomographic image of the catheter sheath 201 at the position is generated.

This can generate the tomographic image corresponding to the tomographic image 614 in FIG. 6B.

If the generation of the tomographic image is completed, the light transmitting and the light receiving are completed, and the rotary operation is completed.

In Step S526, the imaging core 220 is moved so that the optical transmitting and receiving unit 221 is located at the axially center position of the measurement slit portions at the first position which is calculated in Step S523.

In Step S527, the light transmitting and the light receiving are started at the axially center position of the measurement slit portions at the first position, the rotary operation is started, and the tomographic image of the catheter sheath 201 at the position is generated.

This can generate the tomographic image corresponding to the tomographic image 614 in FIG. 6B.

If the generation of the tomographic image is completed, the light transmitting and the light receiving are completed, and the rotary operation is completed.

In Step S528, with regards to the respective measurement slit portions 321 to 324 which are included in the tomographic image generated in Step S525, the heights L2 of the sheets 330 are calculated.

Furthermore, the maximum value and the minimum value are excluded from the calculated heights of the sheets 330, and the average value is calculated with regard to the heights L2 of the remaining two sheets 330.

Similarly, with regard to the respective measurement slit portions 311 to 314 included in the tomographic image generated in Step S527, the heights L2 of the sheets 330 are calculated.

Furthermore, the maximum value and the minimum value are excluded from the calculated heights L2 of the sheets 330, and the average value is calculated with regard to the heights L2 of the remaining two sheets 330.

These processes are performed in Steps S401 and S403. In this manner, it is possible to calculate parameters ($L2_{b0}$, $L2_{f1}$, $L2_{b1}$, and $L2_{f0}$) illustrating the deformation degrees in the measurement slit portions which are required for calculating the myocardial fractional flow reserve (FFR).

Note that, herein, a configuration for obtaining the height (L2) from the bottom surface of the measurement slit portion to the sheet 330 is adopted. However, the imaging apparatus for diagnosis is not limited in this way, and the same process may be performed for a cross-sectional area (S) or a distortion amount of the sheet 330 (L1/W).

As is apparent from the above description, the imaging apparatus for diagnosis according to the present embodiment adopts a configuration in which the multiple measurement slit portions are disposed at the first position and the second position in the axial direction of the probe unit 101 and the sheet 330 is further arranged on the outer peripheral surface of the catheter sheath 201 so as to cover the measurement slit portions.

In this manner, it becomes possible to capture the pressure applied to the probe unit 101 as the deformation of the sheet 330 in the measurement slit portions.

In addition, the generated tomographic image allows the deformation to be analyzed. Accordingly, it becomes possible to calculate the parameters required for calculating the myocardial fractional flow reserve.

As described above, a configuration is adopted so as to calculate the pressure applied to the probe unit 101 without arranging a pressure sensor. In this manner, as compared to a case of arranging the pressure sensor inside the probe unit, it is possible to decrease the diameter of the probe unit and to reduce the cost.

In the above-described first embodiment, when capturing the deformation of the sheet in the measurement slit portions, an influence of a pulse is not particularly considered. However, the imaging apparatus for diagnosis disclosed here may be configured to consider the timing of the pulse.

In general, when a myocardial fractional flow reserve is calculated, it is desirable to use the parameter acquired in a state where the pressure inside a blood vessel is maximized by the pulse.

Therefore, the present embodiment adopts a configuration in which the parameter is extracted by a tomographic image at the timing when the pressure inside the blood vessel is maximized by the pulse.

Hereinafter, referring to FIG. 7, details of the present embodiment will be described.

FIG. 7 is a view schematically illustrating a relationship between the pulse and the deformation of the measurement slit portions.

7a of FIG. 7 illustrates a time series change in the pressure inside the blood vessel when it is assumed that a horizontal axis represents a time period and a vertical axis represents the pressure inside the blood vessel.

As illustrated in 7a of FIG. 7, the pressure inside the blood vessel is significantly changed by the pulse.

7b of FIG. 7 schematically illustrates the deformation of a sheet 330 in measurement slit portions 311 to 314 and 321 to 324.

As illustrated in 7b of FIG. 7, in a case where the pressure inside the blood vessel is increased by the pulse, the sheet 330 in the measurement slit portion varies to a greater deformation degree, as compared to a state before the pressure inside the blood vessel is increased or a state after the pressure inside the blood vessel is decreased.

Therefore, the tomographic images at the respective timings are as illustrated in 7c of FIGS. 7 (701 to 703).

That is, the influence of the pulse causes the deformation degree of the sheet 330 in the measurement slit portions to greatly vary. Therefore, in Step S525 in FIG. 5B, the imaging apparatus for diagnosis according to the present embodiment performs measurement during a predetermined time period including at least a single pulse.

Similarly, in Step S527 of FIG. 5B, the measurement is performed during the predetermined time period (normally, one second or longer) including at least the single pulse.

Furthermore, in Step S528, with regard to the respective measurement slit portions 321 to 324 included in the multiple tomographic images generated in Step S525, the heights (L2) of the sheets 330 are calculated. The tomographic image in which the height of the sheets 330 is minimized (tomographic image corresponding to 702 of 7c in FIG. 7) is extracted for each measurement slit portion.

In this manner, the height (L2) of the sheet 330 at the timing when the pressure inside the blood vessel is maximized by the pulse can be calculated for each measurement slit portion.

Then, the maximum value and the minimum value are excluded from the calculated heights (L2) of the sheets 330 with regard to the four measurement slit portions, and the average value is calculated with regard to the heights (L2) of the remaining two sheets 330.

Similarly, with regard to the respective measurement slit portions 311 to 314 included in the multiple tomographic images generated in Step S527, the heights (L2) of the sheets 330 are calculated. The tomographic image in which the height (L2) of the sheets 330 is minimized (tomographic image corresponding to 702 of 7c in FIG. 7) is extracted for each measurement slit portion.

In this manner, the height (L2) of the sheet 330 at the timing when the pressure inside the blood vessel is maximized by the pulse can be calculated for each measurement slit portion.

Then, the maximum value and the minimum value are excluded from the calculated heights (L2) of the sheets 330 with regard to the four measurement slit portions, and the average value is calculated with regard to the heights (L2) of the remaining two sheets 330.

As is apparent from the above-description, the imaging apparatus for diagnosis according to the present embodiment can calculate the myocardial fractional flow reserve by using the parameter acquired in a state where the pressure inside the blood vessel is maximized by the pulse.

Note that, herein, a configuration for obtaining the height (L2) from the bottom surface of the measurement slit portion to the sheet 330 is adopted. However, the imaging apparatus for diagnosis disclosed here is not limited in this way, and the same process may be performed for a cross-sectional area (S) or a distortion amount of the sheet 330 (L1/W).

In the above-described first embodiment, the measurement slit portion is formed by cutting out the catheter sheath 201, but the imaging apparatus for diagnosis is not limited to this configuration.

A configuration may be adopted in which a member having a shape which can form a gap corresponding to the measurement slit portion adheres to the outer periphery of a catheter sheath 201 and is covered with a sheet 330 thereon.

Note that, in this case, it is desirable to use a member having rigidity higher than that of the sheet 330 as the member adhering to the outer periphery of the catheter sheath 201.

In the above-described first embodiment, four measurement slit portions are configured to be respectively disposed at the first position and the second position. However, without being limited thereto, the imaging apparatus for diagnosis may employ four or more measurement slit portions.

In addition, the above-described first embodiment adopts the configuration in which the average value is calculated after the maximum value and the minimum value are excluded from the parameters indicating the deformation degree of the measurement slit portions, which are respectively calculated at the first position and the second position. However, the imaging apparatus for diagnosis is not limited to the above configuration.

As long as a method is employed in order to increase reliability of the calculated parameter, the parameter may be calculated by any other method.

In addition, in the above-described first embodiment, the measurement slit portions are configured to be disposed at two locations of the first position and the second position. The imaging apparatus for diagnosis disclosed may optionally adopt a configuration in which the measurement slit portions are disposed at three or more positions in the axial direction.

In addition, in the above-described first embodiment, the case of using the OCT as the imaging apparatus for diagnosis has been described. However, without being limited thereto, the imaging apparatus for diagnosis may adopt a configuration of using IVUS to perform the above-described processes.

The detailed description above describes embodiments of a probe and an imaging apparatus representing examples of the probe and imaging apparatus of the present invention. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An imaging apparatus for diagnosis comprising:
a probe unit that includes a sheath and a transmitting and receiving unit located in the sheath, the transmitting and receiving unit transmitting and receiving a signal, the transmitting and receiving unit configured to transmit and receive the signal while rotating inside the sheath in a circumferential direction or while rotating in the circumferential direction and moving in an axial direction, the probe unit including a plurality of deformation portions whose respective cross-sectional shape is deformable in response to an external pressure, the plurality of deformation portions being disposed at different positions of the sheath in the axial direction; and
a computer processor configured to:
calculate at least one parameter at each deformation portion which indicates a deformation degree of the respective deformation portions disposed at the different positions in the axial direction, by using a tomographic image including the deformation portions; and calculate a value corresponding to a myocardial fractional flow reserve, based on the at least one parameter.

2. The imaging apparatus for diagnosis according to claim 1,
wherein each of the deformation portions has a rectangular parallelepiped shape having a predetermined length in the axial direction, and has one surface forming a circumferential surface of the probe unit within the respective deformation portion and the one surface has a rigidity lower than that of other surfaces of the respective deformation portion.

3. The imaging apparatus for diagnosis according to claim 2,
wherein the at least one parameter indicating the deformation degree of the respective deformation portions is one of the following:
a volume of the deformation portion, an area at a predetermined position of the deformation portion in the axial direction, a height of the surface forming the circumferential surface at the predetermined position of the deformation portion in the axial direction, or a distortion amount of the surface forming the circumferential surface at the predetermined position of the deformation portion in the axial direction.

4. The imaging apparatus for diagnosis according to claim 1,
wherein the computer processor is further configured to:
calculate a value corresponding to the myocardial fractional flow reserve as being equal to $(X_{b0} \times X_{f1})/(X_{b1} \times X_{f0})$, where a parameter under atmospheric pressure $P_0$ is $X_{f0}$ and a parameter inside a body lumen is $X_{f1}$ which are calculated with regard to a deformation portion disposed at a first position, from among the plurality of deformation portions disposed at the different positions in the axial direction, and that a parameter under the atmospheric pressure $P_0$ is $X_{b0}$ and the parameter inside the body lumen is $X_{b1}$ which are calculated with regard to a deformation portion disposed at a second position, from among the plurality of deformation portions disposed at the different positions in the axial direction.

5. The imaging apparatus for diagnosis according to claim 1, wherein the processor is further configured to:
extract a tomographic image which includes the respective deformation portion; and
calculate respective center positions in the axial direction of the plurality of deformation portions disposed at the different positions in the axial direction, based on the extracted tomographic image, wherein the at least one parameter is calculated by using a tomographic image generated by rotating the transmitting and receiving unit in the circumferential direction when the transmitting and receiving unit is moved to the respective calculated center positions in the axial direction.

6. The imaging apparatus for diagnosis according to claim 5, wherein the processor is configured to:
generate multiple tomographic images generated by rotating the transmitting and receiving unit in the circumferential direction for a predetermined time period; and
calculate the at least one parameter by using the tomographic image having a greatest deformation degree of the plurality of deformation portions, from among the multiple tomographic images generated by rotating the transmitting and receiving unit in the circumferential direction for the predetermined time period.

7. The imaging apparatus for diagnosis according to claim 1,
wherein the plurality of deformation portions are respectively disposed at a first position in the sheath and at a second position on a further proximal side in the axial direction from the first position, and the plurality of deformation portions are disposed at the respective first position and second position in the circumferential direction.

8. The imaging apparatus for diagnosis according to claim 7, wherein the processor is configured to:
use a parameter indicating a deformation degree of partial deformation portions within the plurality of deformation portions disposed in the circumferential direction.

9. A probe comprising:
a sheath;
a transmitting and receiving unit transmitting and receiving a signal internally positioned in the sheath and configured to transmit the signal to an imaging apparatus for diagnosis to generate a tomographic image by using the signal acquired while rotating inside the sheath in a circumferential direction or while rotating in the circumferential direction and moving in an axial direction; and
a plurality of deformation portions whose respective cross-sectional shape is deformable in response to a pressure applied to the probe, at different positions along the sheath in the axial direction, wherein each deformation portion has a rectangular parallelepiped shape having a predetermined length in the axial direction, and has one surface forming a circumferential surface of the probe within the respective deformation portion, which is configured to have a member having rigidity lower than that of other surfaces of the respective deformation portion.

10. The probe according to claim 9,
wherein the plurality of deformation portions are disposed at a first position in the sheath and at a second position on a proximal side in the axial direction from the first position, and the plurality of deformation portions are disposed at the respective first position and second position in the circumferential direction.

11. A method of calculating a myocardial fractional flow reserve using an imaging apparatus for diagnosis, the method comprising:
inserting the imaging apparatus into a body lumen, the imaging apparatus for diagnosis including a probe unit that includes a sheath and a transmitting and receiving unit located in the sheath, the transmitting and receiving unit transmitting and receiving a signal, the transmitting and receiving unit configured to transmit and receive the signal while rotating inside the sheath in a circumferential direction or while rotating in the circumferential direction and moving in an axial direction, the probe unit including a plurality of deformation portions whose respective cross-sectional shape is deformable in response to an external pressure, the plurality of deformation portions being disposed at different positions of the sheath in the axial direction;
calculating at least one parameter which indicates a deformation degree of the respective deformation portions disposed at the different positions in the axial direction, by using a tomographic image including the deformation portions; and calculating a value corresponding to the myocardial fractional flow reserve, based on the at least one parameter.

12. The method according to claim 11, wherein each of the deformation portions has a rectangular parallelepiped shape having a predetermined length in the axial direction, and wherein the each of the deformation portions has one surface forming a circumferential surface of the probe unit within the respective deformation portion and the one surface has a rigidity lower than that of other surfaces of the respective deformation portion; and wherein the at least one parameter indicating the deformation degree of the respective deformation portions is one of the following:

a volume of the deformation portion, an area at a predetermined position of the deformation portion in the axial direction, a height of the surface forming the circumferential surface at the predetermined position of the deformation portion in the axial direction, or a distortion amount of the surface forming the circumferential surface at the predetermined position of the deformation portion in the axial direction.

13. The method according to claim 11, further comprising:

calculating a value corresponding to the myocardial fractional flow reserve as being equal to $(X_{b0} \times X_{f1})/(X_{b1} \times X_{f0})$, where a parameter under atmospheric pressure $P_0$ is $X_{f0}$ and a parameter inside a body lumen is $X_{f1}$ which are calculated with regard to a deformation portion disposed at a first position, from among the plurality of deformation portions disposed at the different positions in the axial direction, and that a parameter under the atmospheric pressure $P_0$ is $X_{b0}$ and the parameter inside the body lumen is $X_{b1}$ which are calculated with regard to a deformation portion disposed at a second position, from among the plurality of deformation portions disposed at the different positions in the axial direction.

14. The method according to claim 11, further comprising:

extracting a tomographic image which includes the respective deformation portion; and calculating respective center positions in the axial direction of the plurality of deformation portions disposed at the different positions in the axial direction, based on the extracted tomographic image, wherein the at least one parameter is calculated by using a tomographic image generated by rotating the transmitting and receiving unit in the circumferential direction when the transmitting and receiving unit is moved to the respective calculated center positions in the axial direction.

15. The method according to claim 14, further comprising:

generating multiple tomographic images generated by rotating the transmitting and receiving unit in the circumferential direction for a predetermined time period; and calculating the at least one parameter by using the tomographic image having a greatest deformation degree of the plurality of deformation portions, from among the multiple tomographic images generated by rotating the transmitting and receiving unit in the circumferential direction for the predetermined time period.

16. The method according to claim 11, wherein the plurality of deformation portions are disposed at a first position in the sheath and at a second position on a further proximal side in the axial direction from the first position, and the plurality of deformation portions are disposed at the respective first position and second position in the circumferential direction.

17. The method according to claim 16, further comprising:

using a parameter indicating a deformation degree of partial deformation portions within the plurality of deformation portions disposed in the circumferential direction.

* * * * *